United States Patent [19]

Simon et al.

[11] Patent Number: 5,258,279
[45] Date of Patent: Nov. 2, 1993

[54] REVERSIBLE REDOX-CONTROLLED IMAGING METHODS

[75] Inventors: Myron S. Simon, West Newton; Marcis M. Kampe, Brookline; David P. Waller, Lexington, all of Mass.

[73] Assignee: Polaroid Corporation, Cambridge, Mass.

[21] Appl. No.: 708,679

[22] Filed: May 31, 1991

[51] Int. Cl.$^5$ ................................ G03C 1/72
[52] U.S. Cl. .................... 430/559; 430/203; 430/222; 430/224; 430/338; 430/351; 430/542
[58] Field of Search ............. 430/224, 222, 559, 542, 430/351, 338, 203; 503/204

[56] References Cited

U.S. PATENT DOCUMENTS

| | | |
|---|---|---|
| 2,983,606 | 5/1961 | Rogers . |
| 4,536,219 | 8/1985 | Riou et al. . |
| 4,720,449 | 1/1988 | Borror et al. ............ 430/338 |
| 4,960,901 | 10/1990 | Borror et al. ............ 548/207 |

FOREIGN PATENT DOCUMENTS

| | | |
|---|---|---|
| 58-97044 | 6/1983 | Japan . |
| WO8607312 | 12/1986 | PCT Int'l Appl. . |

OTHER PUBLICATIONS

Van de Sande, C. C., Angew. Chem. Int. Ed., Eng. 22 (1983), pp. 191–209.
Neblette, Imaging Processes and Materials, 8th Ed., Van Nostrand Reinhold, N.Y., 1989, Ch. 9, pp. 290–291.
Carpenter, J. W., and Lauf, P. W., "Photothermographic Silver Halide Systems", Research Disclosure, No. 17029, Jun. 1978.

*Primary Examiner*—Charles L. Bowers, Jr.
*Assistant Examiner*—Thorl Chea
*Attorney, Agent, or Firm*—Carol A. Loeschorn

[57] ABSTRACT

A novel class of N-substituted triarylmethane sulfonamides is provided which undergo reversible oxidation into colored form and reversible reduction of the oxidized form into colorless form. Preferred embodiments comprise xanthene sulfonamides having N-aryl substituents, e.g., hydroquinone substituents. These compounds possess redox potentials ranging between about +200 to −500 millivolts and thus are useful as dyes for producing photographic, photothermographic, thermal, and pressure-induced images, as well as being useful as redox indicators in a wide variety of biological and chemical reactions.

19 Claims, No Drawings

REVERSIBLE REDOX-CONTROLLED IMAGING METHODS

BACKGROUND OF THE INVENTION

1. Field of the Invention

This invention relates to novel compounds useful as redox indicators in chemical and biological systems and as dyes in photographic, photothermographic, thermographic, and pressure-sensitive processes. Additionally, it relates to the use of said novel compounds in producing photographic, photothermographic, thermographic, and pressure-induced images.

2. Background Art

Photographic systems employing liquid development to produce the final image as well as photothermographic and thermographic systems utilizing dry processing, that is, processing without the use of liquids, to generate the final image are well known in the art.

For each system, a number of different processes for producing color images have been proposed. See for example, C. C. Van de Sande, Angew. Chem. Int., Ed. Eng. 22 (1983), pp. 191-209 for a discussion of color imaging processes as applied in photographic systems, Neblette, Imaging Processes and Materials, 8th Ed., Van Nostrand Reinhold, N.Y., 1989, Ch. 9, p. 290 for an overview of processes for producing color images applicable in photothermographic systems, and U.S. Pat. No. 4,536,219 which discusses various known processes for forming color images in thermographic applications.

Among the processes of commercial significance for producing color images in photographic systems is the dye developer system. As is now well known and discussed in U.S. Pat. No. 2,983,606, the dye developer system relies upon the use of a molecule comprising a developer moiety such as a hydroquinone or p-aminophenol moiety which is linked usually by an insulating group to a dye or color-shifted dye moiety. The main function of the insulating group is to electronically insulate the dye portion of the molecule such that redox changes within the developer moiety do not affect the chromophoric or colored state of the dye moiety directly. Generally, there is little or no change in color between the oxidized and reduced forms of the dye developers.

In photographic systems for forming color images employing dye developers, a photosensitive element comprising at least one silver halide layer having a dye developer associated therewith (in the same or in an adjacent layer) is developed by applying an aqueous alkaline processing composition. Development of the exposed silver halide results in oxidation of the dye developer to provide an oxidation product which is appreciably less diffusible than the unreacted dye developer, thereby providing an imagewise distribution of diffusible dye developer in terms of unexposed areas of the silver halide layer, which imagewise distribution is then transferred, at least in part, by diffusion, to a dyeable stratum to impart thereto a positive dye transfer image.

Another method for forming a color image, disclosed for use in photographic systems, is described in Japanese Patent Application Laid-Open No. 58/97,044 [83/97,044] of S. Ikeuchi et al which has a Laid-Open date of Jun. 9, 1983. In the method described therein, a photosensitive element is employed which comprises a silver halide emulsion layer and a colored dye such as a substituted triarylmethane sulfonamide which in combination with the emulsion forms a color image. Image formation is effected by imagewise exposing the photosensitive element, developing with a developer in alkaline solution thereby forming an oxidation product of the developer in an imagewise distribution corresponding to the imagewise exposure of the emulsion and reacting the oxidation product of the developer with the colored dye to oxidize the colored dye. The oxidized dye then loses its color irreversibly by hydrolytic reaction with the alkali in the developing solution. The color image is formed by that portion of the colored dye that remains unoxidized and thus is not susceptible to base hydrolysis. It should be noted that if this system starts with the dyes in the photosensitive layers, the light absorption by the dye will reduce the light sensitivity of the system.

Among the processes for producing color images in thermographic and photothermographic systems are those of the metal salt type which employ moderate heating to develop a visible image and which comprise an oxidation-reduction image-forming combination comprising, e.g., an oxidizing agent such as the silver salt of a long chain fatty acid and a color-developing agent as the reducing agent for the silver ions, e.g. indoaniline or phenolic leuco dyes. These and other means for generating dye images in metal salt materials have been described by J. W. Carpenter and P. W. Lauf in their review of "Photothermographic Silver Halide Systems", Research Disclosure, No. 17029, Jun. 1978.

SUMMARY OF THE INVENTION

The present invention is concerned with a class of triarylmethane compounds possessing an N-substituted sulfonamide ring-closing moiety which compounds have reversibly alterable spectral absorption characteristics and which may be reversibly oxidized from a substantially colorless form to a colored compound and the oxidized form reversibly reduced from a colored compound to the original colorless compound. In their colored form, the compounds of this invention absorb radiation extending from the visible region into the near infrared region ($-400-1500$ nm). These compounds exhibit redox potentials ranging between about $+200$ to $-500$ mv and thus are useful as redox indicators in a wide variety of biological and chemical reactions and as dyes in various image recording materials for producing color images. The various image recording materials contemplated by this invention include photographic and photothermal imaging materials as well as thermographic and pressure-sensitive recording materials. In the various image recording materials, the subject compounds may be employed in their colored oxidized form and reduced imagewise to provide the color image or they may be employed in their colorless reduced form and oxidized imagewise to provide the color image.

It is, therefore, one object of the present invention to provide novel compounds and a method for the synthesis thereof.

It is another object of the present invention to provide a method for effecting a color change employing said compounds.

It is a further object of the present invention to provide photographic, photothermographic, thermographic, and pressure-sensitive image recording materials and processes for forming color images employing said novel compounds.

Other objects of the invention will in part be obvious and will in part appear hereinafter.

The invention accordingly comprises the processes involving the several steps and the relation and order of one or more of such steps with respect to each of the others, and the product and compositions possessing the features, properties and the relation of elements which are exemplified in the following detailed disclosure, and the scope of the application of which will be indicated in the claims.

For a fuller understanding of the nature and objects of the invention, reference should be had to the following detailed description.

DETAILED DESCRIPTION OF THE INVENTION

Specifically, the novel compounds of the present invention in their colorless reduced form may be represented by the formula

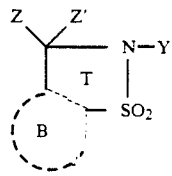

Formula I wherein B represents a carbocyclic ring or rings, e.g., of the benzene or naphthalene series; T represents a 5- or 6-membered ring depending upon whether B contributes 2 or 3 carbons to the ring, T; Y is a moiety selected from

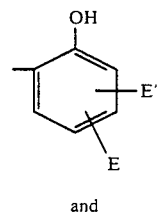
(a)

and

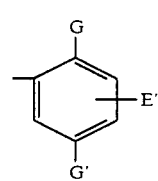
(b)

wherein E, positioned ortho or para to said —OH group, is selected from —OH, —NH$_2$, —NHR', —NR'R" and —NHSO$_2$R' wherein R' and R" each are lower alkyl groups having 1 to 6 carbon atoms or aralkyl groups wherein the aryl portion may be further substituted with alkyl groups having 1 to 24 carbon atoms, and E' is hydrogen or a monovalent group that is substituted on one of the remaining carbon atoms of the aromatic ring; G and G' each are hydroxy or methoxy, provided one is hydroxy and the other is methoxy; and Z and Z' taken individually represent the moieties to complete the chromophoric system of a triarylmethane dye when said N-containing ring, T, is open and Z and Z' taken together represent the bridged moieties to complete the chromophoric system of a bridged triarylmethane dye when said N-containing ring, T, is open, i.e., when the N atom is not attached to the meso carbon atom. Usually, at least one of Z and Z', whether taken individually or together, possesses as an auxochromic substituent a nitrogen, oxygen or sulfur atom or a group of atoms containing nitrogen, oxygen or sulfur.

The substantially colorless compounds of Formula I in the presence of conventionally known oxidizing agents may be reversibly altered from colorless to colored and the colored oxidized form reversibly reduced to the original colorless form using conventionally known reducing agents. The reduced [Reduc] and oxidized [Ox] forms of the subject compounds are illustrated below:

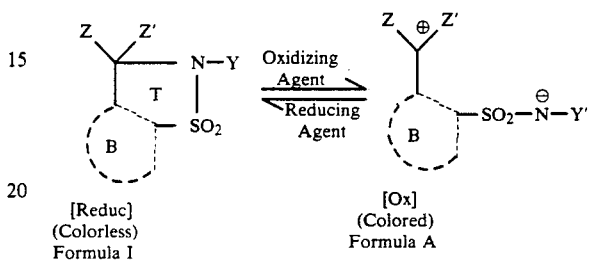

[Reduc]
(Colorless)
Formula I

[Ox]
(Colored)
Formula A wherein B, T, Y, Z and Z' have the same meaning given above and Y' represents the oxidized form of Y; that is, its quinoid form selected from an ortho- or para-benzoquinone, an ortho- or para-quinonemonoimine, an ortho- or para-quinonediimine, and an ortho-or para-quinonesulfonylimine. Preferably, Y is a hydroquinonyl moiety and B represents a benzene ring.

While E' may be any monovalent group, it is preferably a substituent for adjusting the redox potential of the compound and is an electron-donating group or an electron-withdrawing group selected to give a particular potential which may be measured in a conventional manner. Representative electron-donating groups for E' include alkyl groups such as methyl, ethyl, t-butyl and hexyl, alkoxy groups such as methoxy, ethoxy, propoxy and butoxy, and amino, (monoalkyl)amino and (dialkyl)amino wherein said alkyls each contain 1 to 6 carbon atoms. Representative electron-withdrawing groups include cyano, dialkylsulfamoyl, methylsulfonyl, phenylsulfonyl, p-tolylsulfonyl, carboxy, acetyl, carbomethoxy, carbamyl, isothiocyano, benzoyl, trifluoromethyl and halo, e.g., chloro, bromo, fluoro and iodo.

As used herein and as well known in the art, an electron-withdrawing group is a group having a positive sigma value and an electron-donating group is a group having a negative sigma value, the sigma values being defined in terms of Hammett's Equation. In addition to the groups specified above, a number of other groups together with their sigma values are listed in Lang's Handbook of Chemistry and in H. H. Jaffe, a Reexamination of the Hammett Equation, Chem. Reviews, 1953, pp. 222-23.

In the triarylmethane compounds represented in the above formulae, the moieties Z and Z', when taken individually, may be the same or different and typically represent heterocyclic groups containing nitrogen, oxygen or sulfur as the heterocyclic atom, particularly N-heterocyclic groups such as julolidin-3-yl, indol-3-yl, pyrr-2-yl, carbazol-3-yl, and indolin-5-yl wherein the N atom of the indolyl, pyrryl, carbazolyl and indolinyl groups may be substituted with hydrogen or alkyl having 1 to 6 carbon atoms, or the moieties Z and Z' typically may be carbocyclic aryl, particularly phenyl or naphthyl groups which include an appropriately positioned auxochromic substituent, i.e., an atom or group that produces an auxochromic effect, which substituent is usually positioned para to the meso carbon atom. Typically, Z and Z' when taken together represent aryl groups bridged to form a fluorene ring system or aryl groups bridged by a heteroatom, such as, oxygen, sulfur or nitrogen, and particularly represent carbocyclic aryl groups, such as, phenyl groups bridged with a heteroatom, preferably oxygen, sulfur or nitrogen, the nitrogen substituted with hydrogen or an alkyl group having 1 to 6 carbon atoms, which compounds in their oxidized form represent xanthene, thioxanthene or acridine dyes, which dyes possess an auxochromic substituent(s) para to the meso carbon atom, i.e., in the 3-position or in the 3,6-positions or meta and para to the meso carbon atom, i.e., in the 3,7-positions, or a cyclic ring system attached to the 2,3- or 3,4-positions.

Examples of useful auxochromic substituents include —$OR_1$ wherein $R_1$ is hydrogen, alkyl having 1 to 6 carbon atoms, aralkyl having 7 to 15 carbon atoms, alkaryl having 7 to 15 carbon atoms or carbocyclic aryl having 6 to 12 carbon atoms; —$SR_2$ wherein $R_2$ has the same meaning given for $R_1$; —$NR_3R_4$ wherein $R_3$ and $R_4$ each represent hydrogen, alkyl having 1 to 6 carbon atoms, β-substituted ethyl, cycloalkyl having 5 to 7 carbon atoms, aralkyl having 7 to 15 carbon atoms, alkaryl having 7 to 15 carbon atoms, the atoms necessary to complete a cyclic system together with an aryl ring of the bridged system represented by Z and Z', e.g.

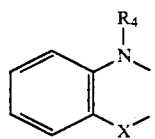

wherein $R_4$ is the same as above, preferably hydrogen or alkyl having 1 to 6 carbon atoms, and X represents carbon, nitrogen or sulfur. $R_3$ and $R_4$ can also be

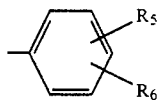

wherein $R_5$ and $R_6$ each are hydrogen alkyl having 1 to 6 carbon atoms, halo such as chloro, bromo, fluoro and iodo, nitro, cyano, alkoxycarbonyl wherein said alkoxy has 1 to 6 carbon atoms, sufonamido (—$NHSO_2R_0$), sulfamoyl (—$SO_2NHR_0$), sulfonyl (—$SO_2R_0$), acyl (—$COR_0$) or carbamyl (—$CPMR_0$) wherein $R_0$ is alkyl having 1 to 6 carbon atoms, benzyl or phenyl and $R_3$ and $R_4$ taken together represent the atoms necessary to complete a heterocyclic ring, e.g. piperidino, pyrrolidino, N-methylpiperidino, morpholino or

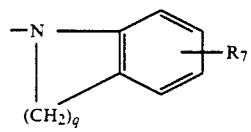

wherein q is an integer 2 to 5 and $R_7$ has the same means as $R_5$,

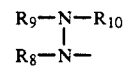

wherein $R_8$ and $R_9$ each are hydrogen, alkyl having 1 to 6 carbon atoms or

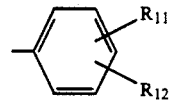

wherein $R_{11}$ and $R_{12}$ have the same meaning as $R_5$ and $R_6$ and $R_{10}$ is —$COR_{13}$, —$CSR_{13}$ or —$SO_2R_{13}$ wherein $R_{13}$ is hydrogen, alkyl having 1 to 6 carbon atoms, phenyl, —$NH_2$, —$NHR_{14}$, —$N(R_{14})_2$ or —$OR_{14}$ wherein $R_{14}$ is hydrogen, alkyl containing 1 to 6 carbon atoms or phenyl. Representative alkyl groups include methyl, ethyl, propyl, butyl and hexyl. Representative β-substituted ethyl groups include β-methoxyethyl and β-2'-tetrahydropyranyloxyethyl. Representative aralkyl groups include phenyl and naphthyl-substituted alkyl, such as, benzyl, phenethyl and naphthylmethyl and representative alkaryl groups include alkyl-substituted phenyl and naphthyl, such as, o-methylphenyl, methylnaphthyl and p-hexylphenyl. Representative carbocyclic aryl groups include phenyl and naphthyl, and representative cycloalkyl groups include cyclopentyl, cyclohexyl and cycloheptyl. It will be appreciated that tho auxochromic substituent(s) will be selected to provide the desired chromophore color when the N-containing ring is opened by breaking the bond between said N atom and the meso carbon atom.

In addition to the auxochromic substituents, Z and/or Z' and/or the ring B of the ring-closing moiety may possess one or more additional substituents as may be desired that do not interfere with the intended utility for the compound. Typical substituents include carboxy; hydroxy; cyano; thiocyano; mercapto; sulfo; nitro; sulfonamido (—$NHSO_2R_0$); sulfamoyl (—$SO_2NHR_0$); sulfonyl (—$SO_2R_0$); acyl (—$COR_0$); carbamyl (—$CONR_0$); halomethyl such as trifluoromethyl; alkyl having 1 to 20 carbon atoms such as methyl, octyl, hexadecyl; alkoxy having 1 to 20 carbon atoms such as methoxy, ethoxy, propoxy and butoxy; alkoxycarbonyl having 1 to 6 carbon atoms such as methoxy- and ethoxycarbonyl; aralkyl having 7 to 15 carbon atoms, for example, phenyl or naphthyl-substituted alkyl such as benzyl, phenethyl and naphthylmethyl; alkaryl having 7 to 15 carbon atoms, for example, alkyl-substituted phenyl or naphthyl such as o-methylphenyl, methylnaphthyl and p-hexylphenyl; aralkyloxy having 7 to 15 carbon atoms, for example, phenyl or naphthyl-substituted alkoxy, such as, benzyloxy, phenethyloxy and naphthylmethyloxy; aryloxy usually containing 6 to 12 carbon atoms such as phenoxy and naphthoxy; thioalkyl groups usually having 1 to 20 carbon atoms such as methylthio, ethylthio and hexylthio; thioaryl and thioaralkyl groups containing up to 15 carbon atoms such as phenylthio, naphthylthio, benzylthio and phenethylthio; halo such as chloro, bromo, fluoro and iodo; amino including mono- and disubstituted amino such as —$NR_{15}R_{16}$ wherein $R_{15}$ and $R_{16}$ each are hydrogen, alkyl having 1 to 20 carbon atoms, aralkyl having 7 to 15 carbon atoms, alkaryl having 7 to 15 carbon atoms, and carbocyclic aryl having 6 to 12 carbon atoms; and a fused substituent such as a fused benzene ring.

Preferred compounds of the present invention are the xanthene compounds represented by Formula II

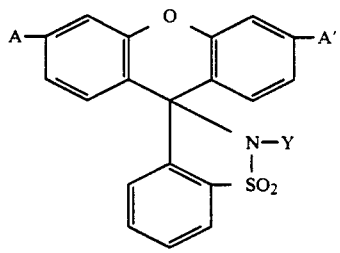

Formula II wherein A and A' are auxochromic substituents and Y has the same meaning given above. Preferred auxochromic substituents are

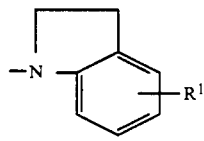

and

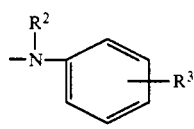

wherein $R^1$ and $R^3$ each are hydrogen or a monovalent radical such as those enumerated above and $R^2$ is alkyl having 1 to 6 carbon atoms.

Useful compounds of this invention include the bridged fluorene compounds represented by Formula III

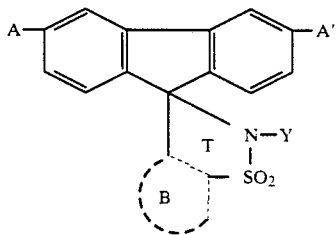

Formula III wherein A and A' are auxochromic substituents and Y, B, and T have the same meaning as above. Preferred auxochromic substituents are substituted and unsubstituted amino substituents such as those enumerated above. Particularly preferred auxochromes are those represented by —NR'R" wherein R' and R" each represent alkyl having 1 to 6 carbon atoms or alkaryl having 7 to 15 carbon atoms. In their oxidized form, the bridged fluorene compounds have substantial absorbance in the near infrared region (700 nm–1500 nm) and are therefore suited for use as imaging dyes in image recording materials where data is stored to be read by an infrared optical character reader, e.g., bar code labels or identification cards where stored information is read by a semiconductor laser or LED.

The subject compounds wherein T is a 5-membered ring may be synthesized by adding a protected dihydroxyaniline or a protected hydroxyaminoaniline to a triarylmethane sulfonyl chloride followed by removal of the protecting group(s) as illustrated in Scheme I below:

Scheme I

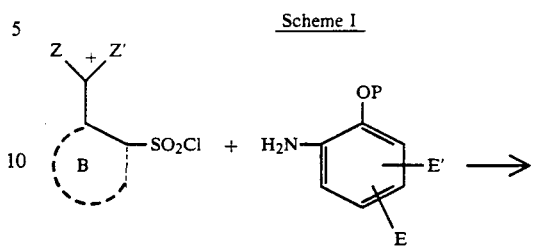

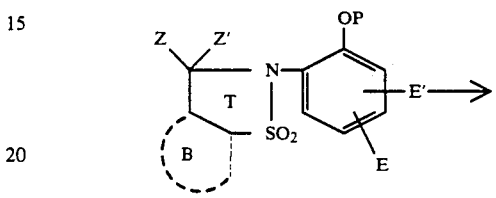

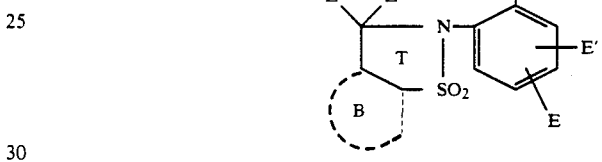

wherein P represents a protecting group, e.g., —CH₃ or

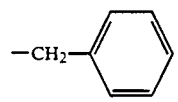

The triarylmethane sulfonyl chloride starting material may be synthesized in a known manner as described, for example, in U.S. Pat. No. 4,283,538 for unbridged triarylmethanes, and in U.S. Pat. Nos. 4,290,950 and 4,304,834 for bridged triarylmethanes. The protected hydroxyaniline and protected hydroxy amino anilines may be synthesized by conventional means, e.g. by selective nitration of the protected ortho- or para-hydroquinone, ortho- or para-quinonemonoimine, ortho- or para-quinonediimine or ortho- or para-quinonesulfonylimine followed by reduction to the aniline as described, e.g., in *Tetrahedron*, 1958, 2 116–121.

Preferably, the subject compounds are prepared according to the novel synthesis of the present invention which comprises reacting a quinone with a triarylmethane sulfonamide as illustrated in scheme II below:

Scheme II

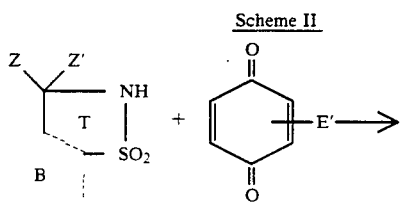

-continued

Scheme II

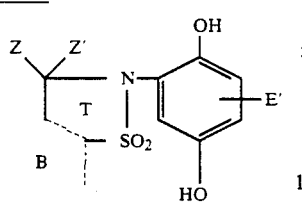

In this novel synthesis a quinone is added in an excess over stoichiometric amounts to a solution of the triarylmethane sulfonamide dissolved in an inert organic solvent, preferably containing a small amount of potassium hydroxide. The quinone may be unsubstituted or substituted with a monovalent radical, and is selected from an ortho- or para-benzoquinone, an ortho- or para-quinonemonoimine, or ortho- or para-quinonediimine or an ortho- or para-quinonesulfonylimine. This reaction may be conducted at room temperature or at elevated temperatures, for example, at a temperature between about 20° and 120° C. Where the reaction product may contain some quinone by-product in admixture with the hydroquinone product, the reaction product may be treated with aqueous sodium hydrosulfite buffered with potassium bicarbonate to convert substantially all of the reaction product to the desired hydroquinone. The triarylmethane sulfonamide wherein T is a 5-membered ring may be prepared as disclosed in the aforementioned U.S. Pat. Nos. 4,283,538, 4,290,950 and 4,304,834. The triarylmethane sulfonamides wherein T is a 6-membered ring can be synthesized in an analogous manner from 2,3-dihydro-3-oxonaphthol-1,8-thiazine-1,1-dioxide which can be synthesized by a method described in Lombardino, J.; *J. Org. Chem.*, 1971, 36 (3), 1843-5.

The following examples are given to further illustrate the present invention and are into intended to limit the scope thereof.

EXAMPLE 1

Preparation of Compound (A) having the formula

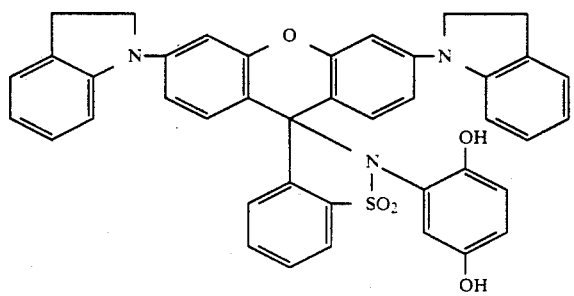

Compound (B) having the formula

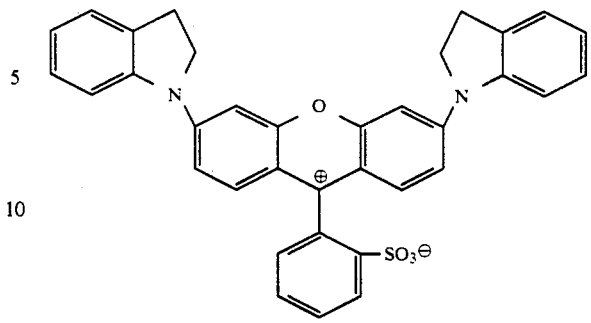

was used as the starting material in step (a) below.

(a) A solution of 3.92 g of phosphorus oxychloride in 60 ml of dichloromethane containing 0.6 ml of 1-methyl-2-pyrrolidinone was added dropwise over a 45-minute period at room temperature to a stirred solution of 6.1 g of Compound (B) in 122 ml of dichloromethane containing 0.12 ml of 1-methyl-2-pyrrolidinone. After addition was complete, 60 ml of dichloromethane was removed by distillation and replaced With fresh dichloromethane. The reaction mixture was then refluxed overnight. Conversion to the corresponding sulfonylchloride (Compound (C)) having the formula

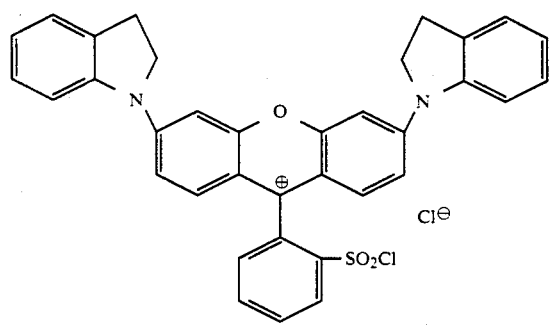

was found to be complete by treating 2 drops of the reaction mixture in acetonitrile with an excess of an alkyl amine which gave an almost colorless product. The reaction mixture was diluted with 60 ml toluene and distilled under reduced pressure. A solution of 50:50 dichloromethane-toluene (120 ml) was added and distillation under reduced pressure was repeated until about 35-40 ml of the reaction mixture remained.

(b) To this mixture was added 7.5 g of 2,5-dimethoxyaniline, 15 ml of pyridine and 1.2 g of 4-dimethylaminopyridine. After stirring overnight, TLC on silica gel using 15:85 methanol-dichloromethane as eluent showed that the reaction was incomplete. An additional 22.5 g of 2,5-dimethoxyaniline was added and the reaction mixture refluxed overnight. The reaction mixture was diluted with water, extracted three times with 5-10% aqueous hydrochloric acid and the solvent removed leaving a dark blue viscous oil. The oil was placed on a silica gel column and the column eluted with a mixture of 8:92 methanol-dichloromethane. The light blue solids obtained were triturated with methanol, and 3.1 g of the N-substituted sulfonamide intermediate (Compound (D)) was obtained as a mixture of its closed colorless form and its open colored form (cyan). The structure was confirmed by NMR and mass spectroscopy.

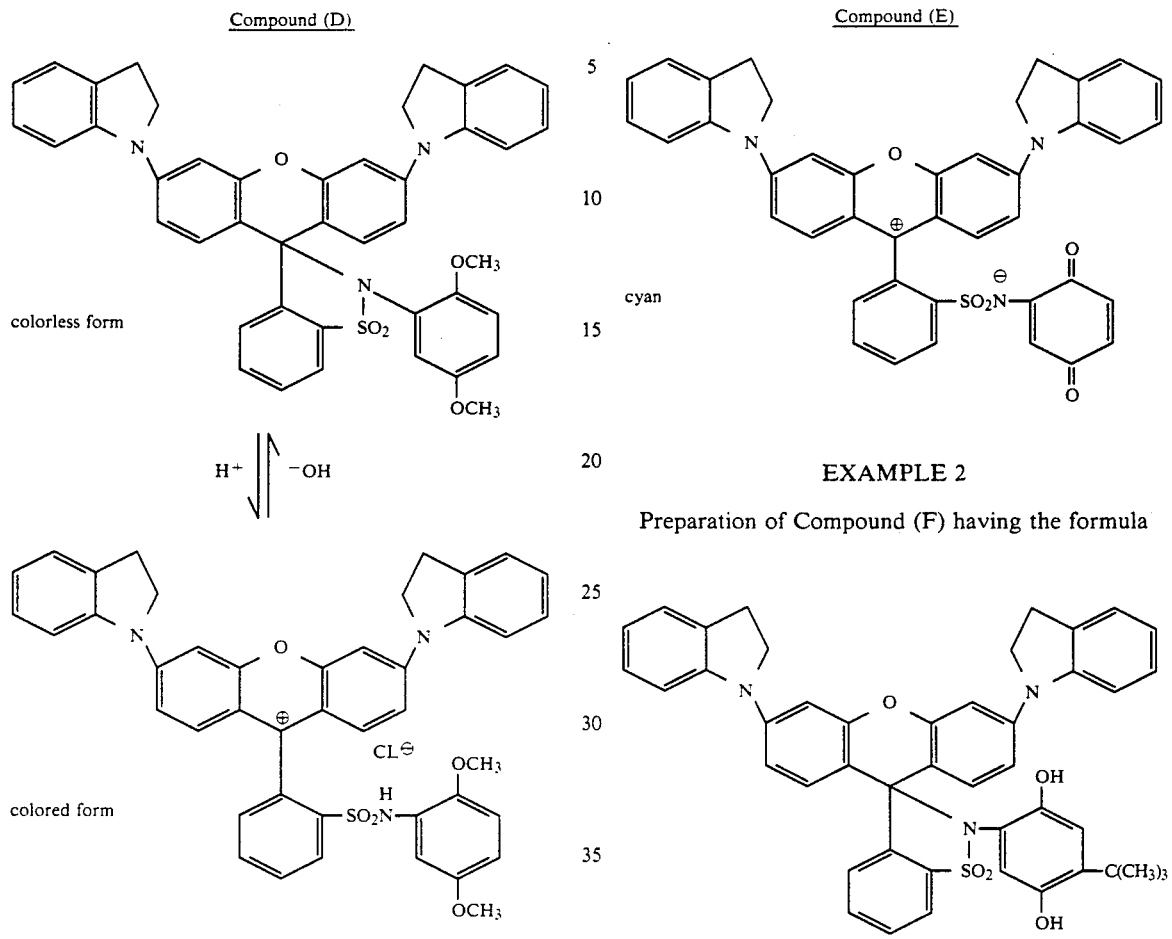

Compound (D)

colorless form

H+ ⇅ -OH colored form

Compound (E)

cyan

EXAMPLE 2

Preparation of Compound (F) having the formula (c) To 80-85 ml of dry dichloromethane under nitrogen was added 3.5 g of boron tribromide dimethylsulfide complex with vigorous stirring followed by the addition of 0.60 g of the product of step (b) above. The resulting deep cyan reaction mixture was refluxed for 3¼ hours and cooled to room temperature. Additional fresh boron tribromide dimethylsulfide (0.60 g) was added and the reaction mixture was stirred under nitrogen at room temperature overnight. The reaction mixture was quenched with water and repeatedly washed with water. The organic layer was separated and concentrated under reduced pressure to give a dark blue solid. The solid was dissolved in dichloromethane, placed on a silica gel column and the column eluted with 2.5:97.5 methanol-dichloromethane. The title compound (A) was recovered as a white solid (0.40 g). The structure was confirmed by NMR and mass spectroscopy. Compound (A) was air oxidized in the presence of 0.5% potassium hydroxide to generate the cyan colored compound, E, having the formula To 2.0 g of the N-hydroquinonyl compound prepared in Example 1 was added 35 ml of tert-butylacetate and 15 ml of dichloromethane. Then 13 drops of concentrated sulfuric acid was added and the reaction mixture heated to 65° C. with stirring. After 30 minutes, 2.0 ml of concentrated sulfuric acid was added to achieve solution of the solids which resulted in a cyan color. The reaction mixture was heated at 65° C. for 45 minutes and then at 80° C. for another 45 minutes. TLC on silica gel using 2:98 acetone-dichloromethane as eluent showed that the reaction was complete. The reaction mixture was cooled, diluted with dichloromethane and washed repeatedly with water. The solvent was removed under reduced pressure to give a blue solid. The solid was dissolved in methanol and the methanol evaporated under vacuum to give 1.3 g of Compound (F) as a colorless solid having a light blue tint. The structure was confirmed by NMR and mass spectroscopy.

EXAMPLE 3

Preparation of Compound (G) having the formula

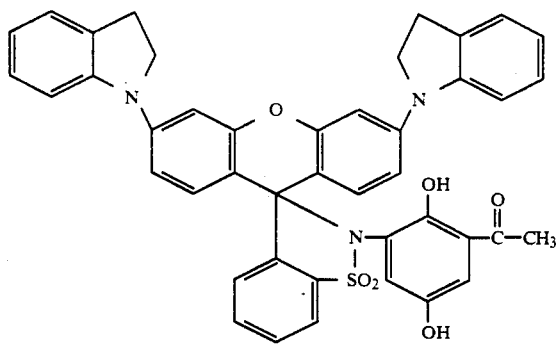

Eleven grams of the xanthene sulfonylchloride compound designated Compound (C) above was prepared according to the procedure given in Example 1 and suspended in approximately 350 ml of dichloromethane. To the suspension was added 7.5 g of 2,5-dibenzyloxy-3-aminoacetophenone and 6 drops of N,N-dimethylacetamide and the reaction mixture stirred at room temperature for 2¼ hours. Then 0.25 g of N,N-para-dimethylaminopyridine and 5.0 ml pyridine were added and the reaction mixture stirred overnight at room temperature. TLC on silica gel using 10:90 methanol/dichloromethane as eluent showed the formation of some of the desired product. The reaction mixture was refluxed for 4 hours, the solvent removed under reduced pressure and the residue extracted with hot toluene. The toluene extract was cooled in an ice water bath, most of the toluene removed under reduced pressure, the residue treated with ether and the ether solution filtered to remove solids. The filtrate was concentrated under reduced pressure, the residue diluted with hexane and the hexane solution filtered. The solids collected were washed with hexane and after drying gave 0.45 g of the N-substituted intermediate of the following formula as an off-white (greenish) solid, Compound (H).

Compound H

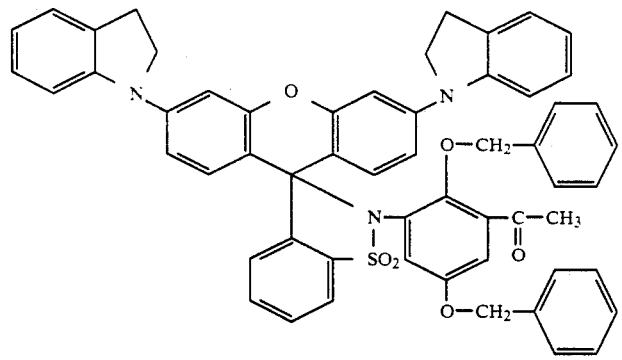

Compound (H) (0.425 g) was dissolved in 225 ml of dichloromethane and HBr gas was passed through the solution for 4 hours at room temperature with stirring. The resulting mixture was blue in color and contained some dark precipitated tars. A small amount of 1,2-dimethoxyethane was added to the reaction mixture followed by a solution of aqueous sodium hydrosulfite buffered with potassium bicarbonate to reduce the quinone. The reaction mixture was stirred until all the tars had redissolved into the organic portion. After washing with fresh aqueous sodium hydrosulfite buffered with potassium bicarbonate and with water, the pale greenish organic portion was decanted and dried over solid sodium hydrosulfite and potassium bicarbonate mixed with a small amount of anhydrous magnesium sulfate. Substantially all of the solvent was removed under reduced pressure and ether was added to the residue. The ether solution was filtered to remove solids, the filtrate reduced to one-half its original volume and hexane was added to the filtrate to obtain separation of off-whit (greenish) solids. The solids were collected by filtration, washed with hexane and dried to give 1.105 g of Compound (G). The structure was confirmed by NMR and mass spectroscopy.

EXAMPLE 4

Preparation of Compound (I) having the formula

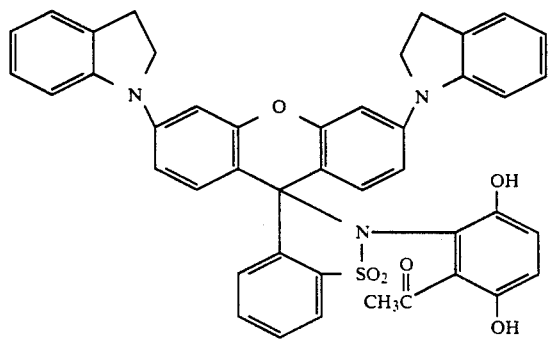

Compound (J) having the formula

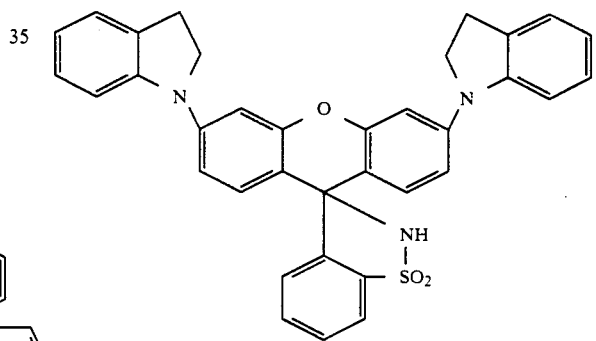

was used as the starting material in step (a) below.

Compound (J) (2.85 g) was dissolved in 200 ml of dichloromethane and 0.75 g of 2-acetyl-p-benzoquinone was added every 30 minutes with vigorous stirring until a total of 4.5 d had been added. The reaction mixture was heated briefly to approximately 40° C., stirred at room temperature overnight and then heated to 40° C. for 2 hours. The reaction mixture, which was green in color, was concentrated and placed on a silica gel column and the column eluted with dichloromethane followed by a 5:95 mixture of methanol/dichloromethane. The fractions containing a mixture of the open quinone form of the title compound having the formula Compound (K)

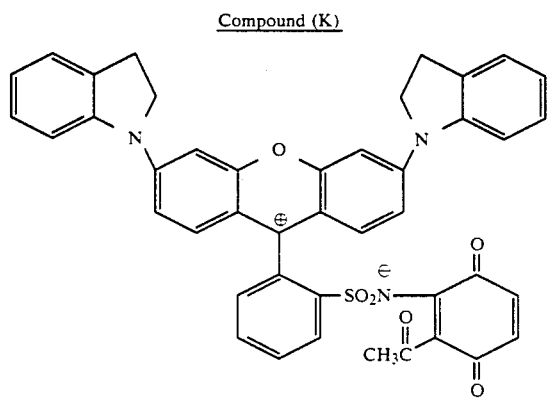

and the closed hydroquinone product were collected and combined. The dark blue product was dissolved in 300 ml of dichloromethane and stirred together with 250 ml of aqueous sodium hydrosulfite buffered with potassium bicarbonate to reduce the quinone. The organic portion was separated and evaporated down to give the crude product. The product was placed on a silica gel column and the column eluted with dichloromethane followed by a 6:94 mixture of acetone-dichloromethane. The title compound (I) (0.8 g) was isolated as an off-white solid. The structure was confirmed by NMR and mass spectroscopy.

EXAMPLE 5

Preparation of Compound (L) having the formula

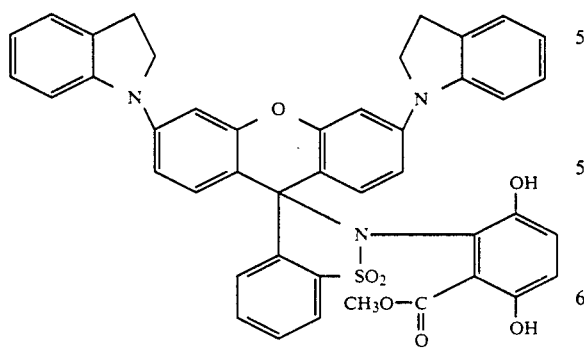

0.6 g of xanthene sulfonamide starting material designated Compound (J) in Example 4 above was added to 5 ml of dichloromethane. One pellet of potassium hydroxide was added to this solution together with an excess of the quinone having the formula

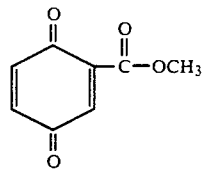

The reaction mixture was allowed to stand at room temperature for 2¼ hours with occasional stirring. During this time, the dark blue quinone addition product formed (Compound (M)) and the sulfonamide starting material disappeared as evidenced by TLC on silica gel using 10:90 methanol-dichloromethane as eluent. Compound (M) having the formula

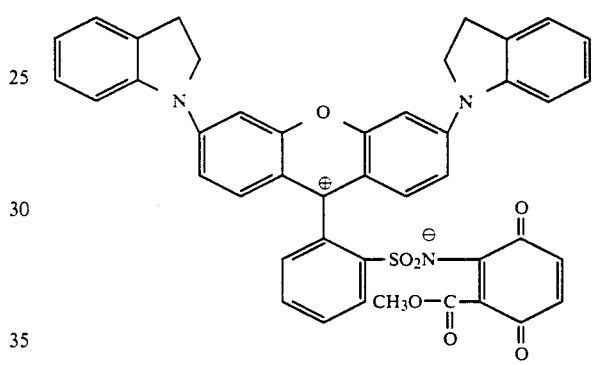

was converted to the title compound by dissolving in dichloromethane, stirring together with aqueous sodium hydrosulfite buffered with potassium bicarbonate. The organic portion was separated and evaporated to give the title compound (L). The structure was confirmed by mass spectroscopy.

EXAMPLE 6

Preparation of Compound (N) having the formula

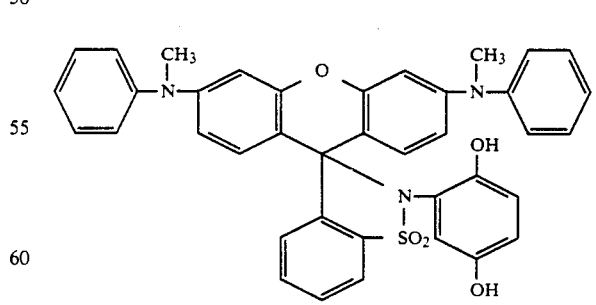

The title compound (N) was prepared according to the procedure given in Example 1 above using Compound (O), having the following formula, as the starting material.

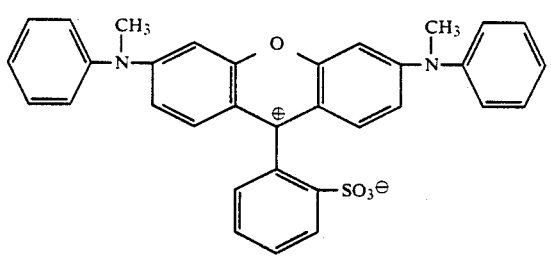
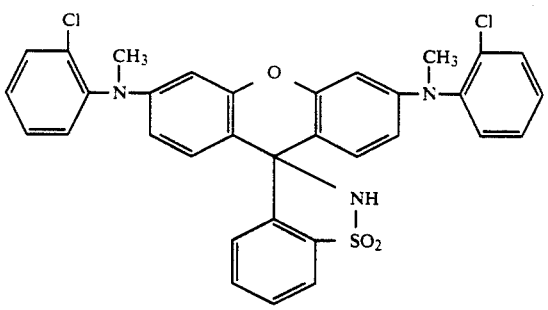

EXAMPLE 7

Preparation of Compound (P) having the formula

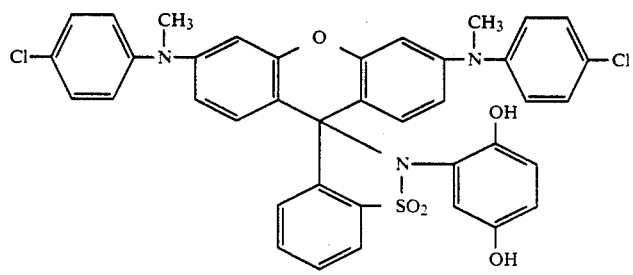

The title compound (P) was prepared according to the procedure given in Example 1 above using Compound (Q), having the following formula, as the staring material

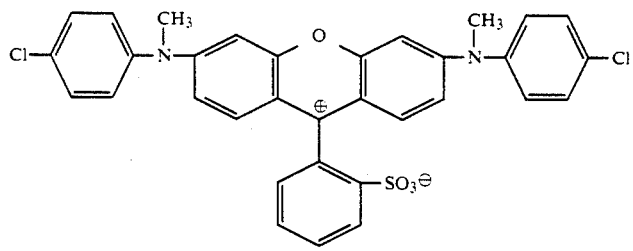

EXAMPLE 8

Preparation of Compound (R) having the formula

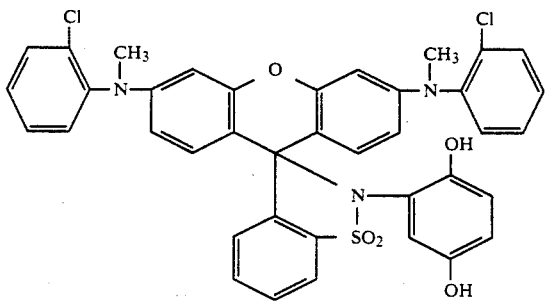

Compound (S), having the formula set out below, was used as the starting material in the following synthetic procedure To 25 ml of dry dimethyl sulfoxide was added 3.49 g of Compound (S), followed by the addition of 1.4 g p-benzoquinone and one pellet (94.7%) of sodium hydroxide. The reaction mixture was heated with stirring under nitrogen to about 120° C. for 30 minutes, and the temperature maintained in the range of 95°–110° C. for 2 hours. A magenta color formed. The reaction mixture was cooled, diluted with 500 ml dichloromethane and washed with several portions of fresh water and with aqueous sodium hydrosulfite. The reaction mixture was reduced to dryness leaving magenta solids which were placed on a silica gel column. Elution with dichloromethane removed the starting material and further elution with 2% acetone in dichloromethane gave the colorless title compound (R). Yield 2.0 g. The structure was confirmed by NMR and mass spectroscopy.

EXAMPLE 9

Preparation of Compound (T) having the formula

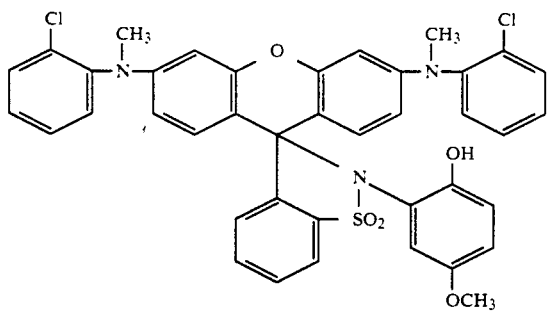

To 1.4 g of the N-hydroquinonyl compound of Example 8 dissolved in 50 ml of dichloromethane was added 0.28 g of potassium carbonate and 3.0 ml of iodomethane. After refluxing the reaction mixture overnight, 30 ml more iodomethane and fresh dichloromethane were added and the reaction mixture refluxed under nitrogen. The addition of 3.0 ml of iodomethane followed by refluxing was repeated several times. Then the reaction mixture was allowed to stand at room temperature over the weekend. The solvent and excess iodomethane were removed under reduced pressure to give a magenta residue. The residue was extracted with dichloromethane leaving most of the inorganic materials behind. The extract was placed on a silica gel column and the column eluted with 2.5% acetone in dichloromethane followed by 5% acetone in dichloromethane. The title compound (T) was collected as an off-white solid with a pink tinge. Yield 0.125 g. The structure was confirmed by NMR and mass spectroscopy.

EXAMPLE 10

Preparation of Compound (U) having the formula

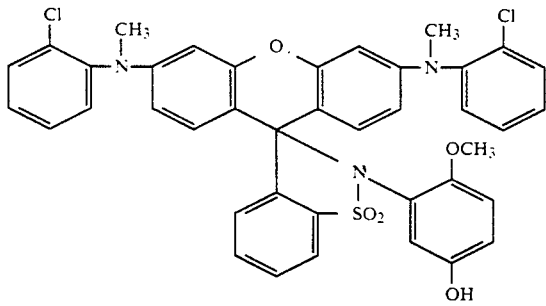

Compound (V) having the formula

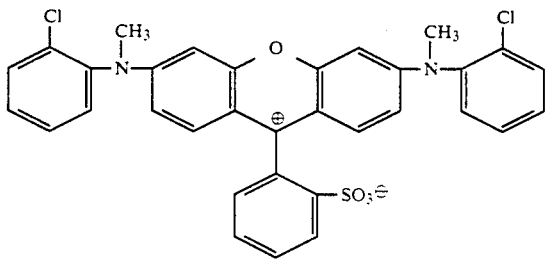

was converted to the corresponding sulfonylchloride and the sulfonylchloride reacted with 2,5-dimethoxyaniline using the procedures described in steps (a) and (b) of Example 1 above to give Compound (W) having the formula

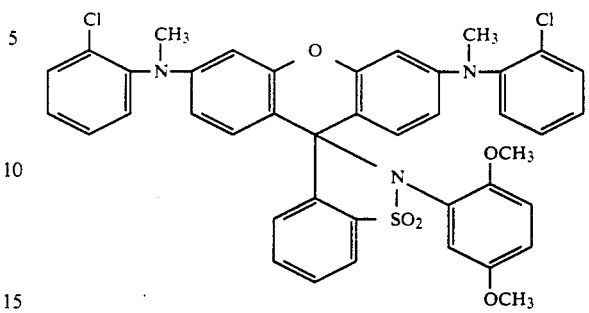

To 7.0 g of Compound (W) dissolved in 90 ml dichloromethane was added 2.9 g of boron tribromide dimethylsulfide complex. The reaction mixture was refluxed for 90 minutes, allowed to stand at room temperature overnight and then refluxed for 3 hours. Additional boron tribromide dimethylsulfide (1.5 g) was added and the reaction mixture refluxed for another hour. After cooling to room temperature, the reaction mixture was quenched with methanol and washed several times with water and dried over anhydrous sodium sulfate. The solvent was removed leaving a magenta tar which was placed on a silica gel column. The column was eluted with dichloromethane, then with 25:75 acetone-dichloromethane. 1.1 g of the title compound (U) was collected as an off-white crystalline solid. The structure was confirmed by NMR and mass spectroscopy.

As noted earlier, the compounds of the present invention are useful for forming color images in imaging recording systems including photographic, photothermographic, thermographic, and pressure-sensitive imaging systems. The image recording materials of this invention comprise a support carrying (a) at least one image dye-providing compound of Formula I or formula A and (b) a developing material in the same or separate layers. The developing material is a material which when contacted with the image dye-providing compound is capable of either oxidizing or reducing the image dye-providing compound, depending upon whether the reduced or oxidized form of the subject compound is employed.

The compounds of Formula I, wherein Y is moiety (a), possess redox potentials which makes them particularly useful as image dye-providing compounds for forming photographic color images processed by wet development. In photographic imaging systems, the colorless form (or colored form) of these image dye-providing compounds usually is disposed in a layer or layers of the photosensitive element other than the layer containing the light-sensitive silver halide emulsion. For example, the compound may be in a layer on one side of the emulsion layer or in two layers, one on either side of the emulsion layer. Preferably, the compound is disposed in a layer on a support and overcoated with the light-sensitive silver halide emulsion layer. If desired, it may be separated from the emulsion layer by a spacer layer and a topcoat may be used over the emulsion layer. Usually, the support carrying the layer of image dye-providing compound is coated with a subcoat layer. If the image dye-providing compound is present in the light-sensitive emulsion layer, the compound preferably is in its colorless form and should be inert, that is photographically innocuous in that it does not adversely affect or impair image formation. If the compound is not photographically innocuous, it may be modified in a manner which does not interfere with the development process in any way or adversely affect the emulsion. It should be apparent that in these systems the image dye-providing compounds should not diffuse from the layer in which they are initially disposed.

Besides monochromatic systems, the image dye-providing compounds of this invention may be employed in photographic systems utilizing multilayer photosensitive elements comprising at least two selectively light-sensitive silver halide emulsion layers having said image dye-providing compounds associated therewith which are processed simultaneously and without separation to provide a multicolor image. In such a structure, interlayers containing scavengers for any auxiliary developers may be used to prevent undesired interactions. Also, filter layers containing, e.g., bleachable filter dyes of the type described in U.S. Pat. Nos. 4,304,833, 4,358,118 and 4,304,834 may be used to control the spectral composition of light falling on the underlying light-sensitive layer. Another useful structure for obtaining multicolor images is the screen type negative described in U.S. Pat. No. 2,968,554 or that described in U.S. Pat. No. 3,019,124.

The silver halide used in the light-sensitive emulsion layer may be a silver chloride, iodide, bromide, iodobromide, chlorobromide, etc. The binder for the halide, though usually gelatin, may be a suitable polymer such as polyvinyl alcohol, polyvinyl pyrrolidone and their copolymers. The support for the photosensitive element preferably is a plastic film, such as cellulose triacetate film, polyethylene terephthalate film, polystyrene film and polyolefin films, e.g., polyethylene and polypropylene films.

The developed silver present in the photosensitive element after image formation and any remaining silver halide may be removed in a conventional manner, for example, by a bleach-fix bath or the developed silver may be bleached and the undeveloped silver halide complexed in situ. In another embodiment, the silver halide emulsion employed may be one which contains low covering power silver in the developed areas so that bleaching is unnecessary. In any of these embodiments, it will be appreciated that the auxiliary silver halide developing agent, silver halide solvent and other reagents employed should be substantially non-staining. In monochromatic systems, it is preferred to remove the silver halide emulsion layer after processing by employing a stripping layer between the layer of image dye-providing compound and the overlying silver halide emulsion layer.

The processing composition employed comprises an aqueous alkaline solution of an auxiliary developing agent and a silver halide solvent. The named ingredients may be present initially in the aqueous medium or may be present initially in the photographic film unit, for example, in the emulsion and/or interlayers as heretofore suggested in the art. Preferably, the auxiliary developer is present in the emulsion layer. When such ingredients are present initially in the film unit, the processing composition is formed by contacting the element with a suitable aqueous medium to form a solution of these ingredients.

The alkali employed may be any of the alkaline materials heretofore employed, such as sodium or potassium hydroxide and like the developing agent and the solvent may be initially in a layer or layers of the film unit.

The silver halide solvent also may be any of the heretofore known materials, such as sodium or potassium thiosulfate, sodium thiocyanate or uracil; also the thioether-substituted uracils, pseudo-uracils and other compounds disclosed and claimed in U.S. Pat. No. 4,126,459; the 1,3-disulfonylalkanes and cycloalkanes of U.S. Pat. Nos. 3,769,014 and 3,958,992, respectively; or the alkanes containing an intralinear sulfonyl group and, e.g., an intralinear N-tosylsulfimido or N-tosylsulfoximido group as disclosed and claimed in U.S. Pat. No. 4,107,176. Also, a silver halide solvent precursor may be used such as those disclosed in U.S. Pat. No. 3,698,898 and as disclosed and claimed in U.S. Pat. No 4,382,119. The choice of silver halide solvent can have an affect on the rate of development as well as the structure of the developed image.

Silver halide developing agents that may be employed as the auxiliary or messenger developer include tertiary butyl hydroquinone, 2,5-dimethyl hydroquinone, methoxyhydroquinone, ethoxyhydroquinone, 4'-methylphenylhydroquinone; pyrogallol and catechols, such as catechol, 4-phenyl catechol and tertiary butyl catechol; aminophenols, such as 4,6-diamino-orthocresol; 1,4-diaminobenzenes, such as p-phenylenediamine, 1,2,4-triaminobenzene and 4-amino-2-methyl-N,N-diethylaniline; ascorbic acid and its derivatives, such as ascorbic acid, isoascorbic acid and 5,6-isopropylidene ascorbic acid and other enediols, such as, tetramethyl reductic acid; hydroxylamines, such as N,N-di-(2-ethoxyethyl)hydroxylamine, N,N-di-(2-methoxyethyl)hydroxylamine and N,N-di-(2-methoxyethoxyethyl)hydroxylamine; and heterocyclic compounds, such as, 1-phenyl-3-pyrazolidone and 4-methyl-4-hydroxymethyl-1-phenyl-3-pyrazolidone.

Usually, the processing composition includes a viscosity-increasing reagent such as a cellulosic polymer, e.g., sodium carboxymethyl cellulose, hydroxyethyl cellulose, carboxymethyl hydroxyethyl cellulose, etc.; an oxime polymer, e.g., polydiacetone acrylamide oxime; or other high molecular weight polymers.

In addition to the aforementioned ingredients, the processing composition preferably contains an inactive quaternary compound such as ethylpyridinium bromide and also may contain antifoggants, preservatives and other materials as conventionally used in the art.

The processing composition may be applied to the photosensitive element, for example, by coating, dipping, spraying or by the use of a rupturable container or pod such as disclosed in U.S. Pat. No. 2,543,181, the container being positioned between the photosensitive element and a spreader sheet so as to be capable upon rupturing of spreading its contents in a substantially uniform layer.

The spreader sheet preferably carries a layer of an acid-reacting reagent to lower the environmental pH following dye image formation in order to increase image stability. These layers may comprise polymers which contain acid groups, e.g., carboxylic acid and sulfonic acid groups, which are capable of forming salts with alkali metals or with organic bases; or potentially acid-yielding groups such as anhydrides or lactones. Preferably the acid polymer contains free carboxyl groups, and preferably, a "timing" layer is coated over the polymeric acid layer in order to control or "time" the pH reduction so that it will not be premature and interfere with the development process. Suitable "timing" layers are described with particularity in U.S. Patent Nos. 3,362,819; 3,419,389; 3,421,893; 3,455,686; and 3,575,701.

In addition to the aforementioned layers, the photosensitive and spreader elements may contain additional layers as commonly used in the art, such as a layer of antihalation dye, and/or a layer of filter dye arranged between differentially color-sensitive emulsion layers, provided the dyes used become decolorized during photographic processing or otherwise do not introduce color in the final image.

As an illustration of the utility of the subject compounds in the production of photographic images, photosensitive elements were prepared employing the compound of Example 1 and the compound of Example 8.

EXPERIMENTS 1 AND 2

These elements were prepared by coating a gelatin subcoated transparent polyethylene terephthalate film base with the following layers:

(a) 10 mgs/ft$^2$ of poly-4-vinylpyridine containing about 100 mgs/ft$^2$ of the compound of Example 1 (or about 90 mgs/ft$^2$ of the compound of Example 8);

(b) a stripping layer;

(c) a layer of a gelatino silver iodobromide emulsion layer containing 30 mgs/ft$^2$ of silver and 15 mgs/ft$^2$ of 4'-methylphenylhydroquinone; and (d) a topcoat layer of gelatin containing succindialdehyde A second element was prepared as a spreader sheet which comprised a transparent polyethylene terephthalate film base carrying the following layers:

(1) a polymeric acid layer and (2) a polymeric spacer (timing) layer.

The photosensitive elements were given an exposure to white light of 2 mcs and superposed with said spreader elements. A layer of an aqueous alkaline processing composition approximately 0.0032 inch thick was distributed between said elements by passing the film units between a pair of pressure-applying rollers in the dark. The processing composition comprised the following ingredients:

| | |
|---|---|
| Water | 100 cc |
| Potassium hydroxide | 5 g |
| Carboxymethyl hydroxyethyl cellulose | 3 g |
| Benzotriazole | 0.25 g |
| Ethylpyridinium bromide | 1 g |
| Silver halide solvent (designated in the following TABLE) | 1.5 g |

After applying the processing composition, the film units were imbibed for about 5 minutes in the dark and then the spreader sheets were removed. The maximum and minimum transmission densities were measured before and after stripping the silver halide emulsion and topcoat layers from the processed photosensitive elements via the stripping layer. The densities measured for the cyan image obtained with the compound of Example 1 and for the magenta image obtained with the compound of Example 8 are set forth in the Table below.

TABLE

| Silver Halide Solvent: | 6-Methyluracil | 6-Methylthio-methyluracil | 1,3-Dithiane Disulfone |
|---|---|---|---|
| | Compound of Ex. 1 (with emulsion layer) | | |
| Red Dmax | 1.25 | 1.46 | 0.83 |
| Red Dmin | 0.46 | 0.68 | 0.12 |
| | (without emulsion layer) | | |
| Red Dmax | 0.93 | 1.22 | 0.85 |
| Red Dmin | 0.22 | 0.27 | 0.08 |
| | Compound of Ex. 8 (with emulsion layer) | | |
| Green Dmax | 1.80 | 2.02 | 1.90 |
| Green Dmin | 0.36 | 0.54 | 0.40 |
| | (without emulsion layer) | | |
| Green Dmax | — | — | 1.70 |
| Green Dmin | — | — | 0.19 |

Rather than employing the colorless reduced form of the subject image dye-providing photographic materials to form color imagewise as in the above photosensitive elements, it will be appreciated that the colored oxidized form may be used by coating a dye-quinone layer adjacent to the silver halide emulsion layer. Exposure and development of the silver halide layer would leave an image in unused developer that could migrate over to reduce and decolorize the dye-quinone imagewise. Peeling off the silver/silver halide layer would leave a dye image in the dye-quinone layer which would be a negative image. In this embodiment, the processing composition should have a relatively low pH and the developer should be capable of reducing the quinone moiety at that pH.

Also, a positive image could be obtained by further processing. For example, the just described negative image could be bleached by treatment with sulfite, then re-oxidized using an oxidant of potential sufficient to oxidize the hydroquinone, but not strong enough to oxidize the sulfo-hydroquinone.

Photothermographic and thermographic elements, because they are processed by heat, are capable of oxidation/reduction reactions encompassing a wider range of redox potentials than conventional photographic systems processed by wet development. Thus, the compounds of Formula I, wherein Y is either moiety (a) or moiety (b), possess redox potentials within the range of +200 to −500 mv making them useful as image dye providing compounds for forming both photothermographic and thermographic color images The method of forming a photothermographic or thermographic color image according to the present invention comprises heating, generally in the range of 100° C. to 160° C. to develop a visible image and which comprises a heat-induced oxidation/reduction image-forming combination between a compound of this invention and an oxidizing or reducing agent, depending on whether the compound of this invention is used in its colorless, reduced form or its colored, oxidized form.

The photothermographic imaging system contemplated by this invention preferably starts with the compounds of this invention in their colorless reduced form and additionally includes, in a catalytic amount, a photosensitive compound such as a light-sensitive silver halide which requires an imagewise exposure to light to form a latent image followed by overall heating to develop the final image. The latent image catalyzes the heat-induced oxidation/reduction reaction between the oxidizing agent and the compounds of this invention to form a color image corresponding to the exposure. The oxidizing agent for use in such photothermal systems is a light-sensitive organic metal oxidizing material and is preferably the metal salt of a long chain fatty acid such as silver or ferric behenate or stearate.

Photothermographic recording materials using the compounds of this invention can be prepared in accordance with such procedures as disclosed in the aforementioned Research Disclosure No. 17029, issued June 1978.

The thermographic system contemplated by this invention consists of heating the image recording material in an imagewise fashion, by any means known in the art, to initiate the oxidation/reduction reaction which results in a color image. Oxidizing agents for use in thermographic systems include the light insensitive organic metal oxidizing materials such as described above for use in photothermal systems and nitrate salts as known in the art and discussed, for example, in European Patent Application, Publication No. 0181085, publication date May 14, 1986.

Reducing agents for use in thermographic systems using the image-dye providing compounds of this invention include hydroxylamines as discussed by S. Fujita and K. Sanu, J. Org. Chem., 44, 2647 (1979) and any conventionally known reducing agents. Thermographic recording materials using the compounds of this invention can be prepared according to such procedures as disclosed in the aforementioned European Patent Application, Publication No. 0181085, publication date May 14, 1986.

In photothermographic imaging systems, the colorless form (or colored form) of these image dye-providing compounds is usually disposed in a layer or layers of the photosensitive element containing the light-sensitive silver halide and light-insensitive metal source. Preferably, the compound of this invention, the photosensitive silver halide, and the light-insensitive metal source are dispersed in a binder and coated together in one layer on a suitable support. Alternatively, the image dye-providing compound may be coated on an adjacent layer provided the dye is in close enough proximity to the reducible metal source so that the oxidation/ reduction can proceed. A subcoat layer may be coated on the support and a transparent topcoat layer can be added and is generally desired.

In thermographic systems, the image dye-providing compound is usually dispersed in a suitable binder together with the oxidizing or reducing agent, e.g., silver or ferric behenate, and coated together in one layer on a suitable support, although each may be coated as a separate layer. A subcoat and/or a topcoat may be added as heretofore known in the art.

In addition to monochromatic systems, the image dye-providing compounds of this invention may be employed in photothermographic systems utilizing multilayer photosensitive elements comprising at least two selectively light-sensitive silver halide emulsion layers having said image dye-providing compounds associated therewith which are processed simultaneously and without separation to provide a multicolor image.

The silver halide used in the light-sensitive emulsion layer may be any photosensitive silver halide such as, silver chloride, iodide, bromide, iodobromide, chlorobromide, etc. and may be prepared in situ or ex situ. The silver halide may be chemically sensitized using a known method for conventional type photographic light-sensitive materials or by using certain classes of dyes, e.g., merocyanine dyes containing a thiohydantoin, which have been found particularly useful in photothermographic systems such as described in Research Disclosure No. 17029, issued June 1978.

As is generally required in thermal systems, the organic metal oxidizing material should be relatively light-stable and is generally an organic metal salt or salt complex as heretofore known in the art. The usual metal is silver, although other metals can be used, e.g., copper, mercury, and iron. Any organic compound known in the art to be useful for forming the organic metal salt may be employed, see, e.g., those described in U.S. Pat. No. 4,729,942. The preferred choice comprises long chain carboxylic acids such as behenic and stearic acids. See U.S. Pat. No. 4,260,677 for useful silver salt complexes.

The binder for use in photothermal and thermal systems is preferably polyvinyl butyral, but may be any suitable polymer such as cellulose acetate, polystyrene, polyvinyl alcohol, polyvinyl pyrrolidone and their copolymers.

The support for the thermal elements must necessarily be able to withstand the heat required for processing the image, and any suitable support can be employed such as described in the aforementioned Research Disclosure No. 17029, issued June 1978. Depending upon whether the color is to be viewed by transmission or reflection, the support may be transparent or opaque.

Additionally, the photothermographic and thermographic systems of this invention may include other materials heretofore suggested in the art. Toning agents may be added and are generally desired, particularly when they function as transfer agents, although they are not necessary. The preferred toning agent is phthalazinone (PAZ), but other toning agents can be used. Antifoggants can be added, and are generally desired particularly in photothermographic systems, mercury salts being the preferred choice, but other antifoggants known in the art can be employed. Other photographic addenda, e.g., coating said, activators and the like may be added as desired but are not essential.

Also, the photosensitive elements may contain additional layers as commonly used in the art, such as a layer of antihalation dye, and/or a layer of filter dye arranged between differentially color-sensitive emulsion layers, provided the dyes used become decolorized during photothermographic processing as described, for example, in U.S. Pat. No. 3,769,019.

As illustrations of the utility of the subject compounds in the production of thermal images, photosensitive and thermographic elements were prepared employing the compound of Example 1 and Example 2.

EXPERIMENT 3

A photothermographic element was prepared using the Compound of Example 1 as follows:

The light-sensitive silver bromide component was made by combining 4.25 g of a 10% bromide solution, made by dissolving 1.7 g $NiBr_2 \cdot 3H_2O$ in 8.3 g of methanol, with 46.89 g of a silver behenate full soap (2.87% silver in 2-butanone) solution, and 33.15 g 2-butanone to which was added 0.05 g of mercury acetate.

The coating formulation was prepared by mixing in an attritor:

| | |
|---|---|
| Silver behenate full soap (2.87% silver in 2-butanone) | 0.311 g |
| 10% Polyvinylbutyral resin (B-76) (in 2-butanone) | 1.330 g |
| 10% Phthalazinone | 0.120 g |

| | |
|---|---|
| (in 2-butanone) | |
| Light-sensitive silver bromide containing Hg$^{+2}$ | 0.27 g |
| Compound of Example 1 | 0.028 g |

The resulting composition was rod coated with a No. 55 rod to 5 ml wet thickness on a gelatin subcoated transparent polyethylene terephthalate film base, dried at room temperature and then heated at 70° C. for 5 seconds.

The resulting photothermographic element was exposed to a Xenon strobe and processed by heating at 115° C. for 15 seconds. The Dmin and Dmax are reported in the following Table.

TABLE

| | Red | Green | Blue |
|---|---|---|---|
| Dmin | 0.23 | 0.11 | 0.11 |
| Dmax | 2.20 | 1.02 | 1.00 |

EXPERIMENTS 4 AND 5

Thermographic elements were prepared using the Compounds of Example 1 and Example 2 as follows:

The silver behenate dispersion used contained 1.2% silver and was prepared by ball milling silver behenate half soap and 2-butanone.

The coating formulations were prepared by mixing:

| | Experiment 4 | Experiment 5 |
|---|---|---|
| Silver behenate dispersion | 0.316 g | 0.275 g |
| 2.5% Celulose acetate (in 2-butanone) | 1.0 g | 1.0 g |
| Acetone | 0.7 g | 0.7 g |
| Compound of Example 1 | 0.01 g | — |
| Compound of Example 2 | — | 0.012 g |

The resulting formulations were each rod coated with a No. 38 rod to 3.42 ml wet thickness on a gelatin subcoated transparent polyethylene terephthalate film base and dried at room temperature.

The resulting thermographic elements were each heated on a hot plate at 120° C. for 20 seconds. The Dmin and Dmax obtained are reported in the following Table.

TABLE

| | Red | Green | Blue |
|---|---|---|---|
| | Experiment 4 | | |
| Dmin | 0.10 | 0.05 | 0.04 |
| Dmax | 0.60 | 0.35 | 0.30 |
| | Experiment 5 | | |
| Dmin | 0.09 | 0.06 | 0.05 |
| Dmax | 0.81 | 0.40 | 0.75 |

EXPERIMENTS 6 AND 7

Thermographic elements were prepared with the Compound of Example 1 using copper and ferric stearates as the reducible metal source.

The copper stearate dispersion was prepared by combining and mixing in an attritor:

| | |
|---|---|
| Copper (II) stearate | 400 g |
| Polyvinylbutyral (B-76) | 40 g |
| 2-Butanone | 2,200 g |

The coating formulation was prepared by mixing:

| | |
|---|---|
| Copper stearate dispersion | 0.33 g |
| Phthalazinone | 0.011 g |
| 2-Butanone | 1.0 g |
| 10% Polyvinylbutyral (B-76) (in 2-butanone) | 0.06 g |
| Compound of Example 1 (dissolved in 0.06 g dimethylformamide) | 0.010 g |

The ferric stearate dispersion was prepared by combining:

| | |
|---|---|
| Ferric Stearate | 50 g |
| Polyvinylbutyral (B-76) | 5 g |
| 2-Butanone | 300 g | and ball milling for 24 hours.

The coating formulation was made by combining:

| | |
|---|---|
| Ferric stearate dispersion | 1.0 g |
| 10% Phthalazinone (in 2-butanone) | 0.11 g |
| 2-Butanone | 0.50 g |
| 10% Polyvinylbutyral (B-76) (in 2-butanone) | 1.0 g |
| Compound of Example 1 (dissolved in 0.2 g dimethylformamide) | 0.035 g |

The above coating formulations were each rod coated with a No. 34 rod to 3 ml wet thickness on separate gelatin subcoated transparent polyethylene terephthalate film bases and dried at room temperature. The resulting thermographic elements were heated on a hot plate at 120° C. for 3 minute and the Dmin and Dmax were measured. The measured values are reported in the following Table.

TABLE

| Experiment 6 (Copper Stearate) | | | |
|---|---|---|---|
| | Red | Green | Blue |
| Dmin | 0.12 | 0.04 | 0.05 |
| Dmax | 0.98 | 0.31 | 0.22 |

| Experiment 7 (Ferric Stearate) | | | |
|---|---|---|---|
| | Red | Green | Blue |
| Dmin | 0.19 | 0.14 | 0.17 |
| Dmax | 0.65 | 0.27 | 0.28 |

The compounds of this invention could also be employed to produce direct photothermographic positive images, as described for example in U.S. Pat. No. 3,589,901.

Additionally, rather than employing the colorless reduced form of the subject image dye-providing photothermal materials to form color imagewise as in the above described photosensitive elements, it will be appreciated that the colored form may be used. This type of system would require a reducing agent to reduce and decolorize the dye either image- or anti-imagewise.

As mentioned above, the image-dye providing compounds of this invention can also be utilized in pressure-sensitive recording systems. Pressure-sensitive recording materials incorporating the image dye-forming compounds of this invention can be prepared according to such procedures as disclosed in European Patent Application, Publication No. 0177317, publication date Sep. 30, 1985 and U.K. Patent Application GB 2192637, publication date Jan. 20, 1988 and references cited therein.

One such pressure-sensitive system discussed in the above cited European Patent Application, Publication No. 0177317, and in which the image forming dyes of this invention can be employed, uses a topsheet coated with micro-encapsulated benzoyl peroxide and a bottom sheet coated with an image-forming dye precursor which can be oxidized to form a dye when the microcapsules of benzoyl peroxide are ruptured imagewise.

The process of this invention for generating a color change, that is, the process of reversibly oxidizing the N-substituted triarylmethane sulfonamides from a substantially colorless form to a colored form and reversibly reducing the oxidized form from a colored compound to a colorless compound make the compounds of this invention particularly suited for use as redox indicators. Since the compounds of this invention encompass a broad range of redox potentials, their application as redox indicators encompasses a wide variety of biological and chemical analytical techniques. Included in these techniques are processes for determining a component in a biological system such as that disclosed and claimed in the co-pending U.S. patent application of F. A. Meneghini and P. S. Palumbo, Ser. No. 708,472 filed concurrently herewith, and processes for determining the quantity of an inorganic species in a material such as that described by J. L. Bernal et al, *Talanta*, 1990, 37, 931–936, for the determination of selenium in animal fodder. A discussion of redox indicators and their use in quantitative analysis can be found in A. Vogel, *Vogel's Textbook of Quantitative Inorganic Analysis*, 4th Ed., Longman, N.Y., ch. 33 pp. 292–296 (1978).

Since certain changes may be made in the herein-defined subject matter without departing from the scope of the invention herein involved, it is intended that all matter contained in the above description should be interpreted as illustrative and not in a limiting sense.

What is claimed is:

1. An image-recording material which comprises a support carrying (a) an image dye-providing compound of the formula

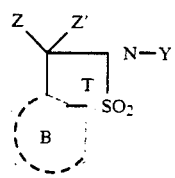

Formula I or

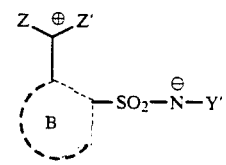

Formula A wherein B is a carbocyclic ring or rings; T is a 5- or 6-membered ring; Y is a moiety selected from

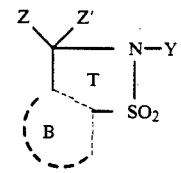

Formula I wherein E, positioned ortho or para to said —OH group, is selected from —OH, —NH₂, —NHR', —NR'R" and —NHSO₂R' wherein R' and R" each are lower alkyl groups having 1 to 6 carbon atoms or aralkyl wherein the aryl portion may be substituted with alkyl groups having 1 to 24 carbon atoms, and E' is hydrogen or a monovalent group that is substituted on one of the remaining carbon atoms; G and G' each are hydroxy or methoxy, provided one is hydroxy and the other is methoxy; and Z and Z' taken individually represent the moieties to complete the chromophoric system of a triarylmethane dye when said N-containing ring, T, is open and Z and Z' taken together represent the bridged moieties to complete the chromophoric system of a bridged triarylmethane dye when said N-containing ring, T, is open; and Y' represents the quinoid form of Y; and (b) in the same or a separate layer, a developing material capable of either oxidizing said Y moiety whereby said compound is rendered colored or reducing said Y' moiety whereby said compound is rendered colorless.

2. An image-recording material as defined in claim 1 wherein said T is a 5-membered ring.

3. An image-recording material as defined in claim 2 wherein said Z and Z' of said image dye-providing compound taken together are represented by

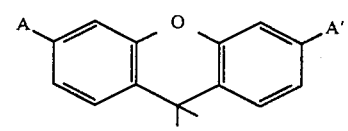

wherein a and A', the same or different, each represent an auxochromic substituent.

4. An image-recording material as defined in claim 3 wherein B is a benzene ring.

5. An image-recording material as defined in claim 4 wherein A is the same as A'πand is represented by

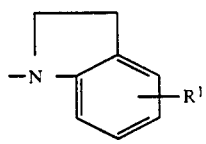

wherein R' is hydrogen or a monovalent radical.

6. An image recording material as defined in claim 4 wherein A is the same as A' and is represented by

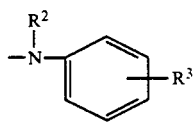

wherein $R^2$ is alkyl having 1 to 6 carbon atoms and $R^3$ is hydrogen or a monovalent radical.

7. An image recording material as defined in claim 1 wherein said Z and Z' of said image dye-providing compound taken together are represented by

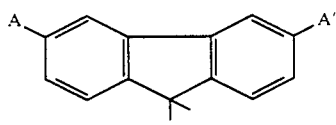

wherein A and A', the same or different, each represent an auxochromic substituent.

8. An image recording material as defined in claim 7 wherein A is the same as A' and is represented by —NR'R" wherein R' and R" each represent alkyl having 1 to 6 carbon atoms or alkaryl having 7 to 15 carbon atoms.

9. An image-recording material as defined in claim 1 wherein said developing material comprises a photosensitive silver halide emulsion which optionally contains an auxiliary silver halide developing agent.

10. An image recording material as defined in claim 9 wherein Y is represented by

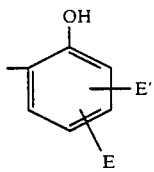

wherein E, positioned ortho or para to said —OH group, is selected from —OH, —NH$_2$, —NHR', —NR'R" and —NHSO$_2$R' wherein R' and R" each are lower alkyl groups having 1 to 6 carbon atoms and E' is hydrogen or a monovalent group that is substituted on one of the remaining carbon atoms.

11. An image-recording material as defined in claim 10 wherein said support is a transparent support carrying in order, a layer of said image dye-providing compound, a stripping layer and a layer of said photosensitive silver halide emulsion which optionally contains an auxiliary silver halide developing agent.

12. A recording material as defined in claim 11 wherein a topcoat layer is coated over said emulsion layer.

13. An image-recording material as defined in claim 9 wherein said photosensitive silver halide is present in a catalytic amount and said developing material additionally includes a light-insensitive organic metal salt oxidizing compound.

14. An image-recording material as defined in claim 13 wherein said light-insensitive organic metal salt is a metal salt of a long chain fatty acid.

15. An image-recording material as defined in claim 14 wherein said metal salt is a silver salt of a long chain fatty acid.

16. An image-recording comprising a support carrying
(a) an image dye-providing compound of the formula

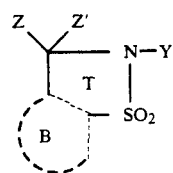

Formula 1 wherein B is a carbocyclic ring or rings; T is a 5- or 6-membered ring; Y is a moiety selected form

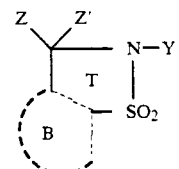

Formula 1 wherein E, positioned ortho or para to said —OH group, is selected from —OH, —NH$_2$, —NHR', —NR'R" and —NHSO$_2$R' wherein R' and R" each are lower alkyl groups having 1 to 6 carbon atoms or aralkyl wherein the aryl portion may be substituted with alkyl groups having 1 to 24 carbon atoms, and E' is hydrogen or a monovalent group that is substituted on one of the remaining carbon atoms; G and G' each are hydroxy or methoxy, provided one is hydroxy and the other is methoxy; and Z and Z' taken individually represent the moieties to complete the chromophoric system of a triarylmethane dye when said N-containing ring, T, is open and Z and Z' taken together represent the bridged moieties to complete the chromophoric system of a bridged triarylmethane dye when said N-containing ring, T, is open; and
(b) int eh same or a separate layer, a developing material capable of oxidizing said Y moiety whereby said compound is rendered colored.

17. An image-recording material comprising a support carrying
(a) an image dye-providing compound of the formula

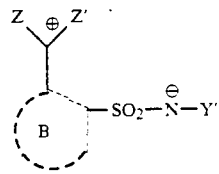

Formula A wherein B is a carboxyclic ring or rings; T is a 5- or 6-membered ring; Y' is the quinoid form of Y; Y is a moiety selected from Formula I

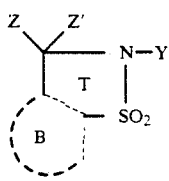

wherein E, positioned ortho or para to said —OH group, is selected from —OH, —NH₂, —NHR', —NR'R" and —NHSO₂R' wherein R' and R" each are lower alkyl groups having 1 to 6 carbon atoms or aralkyl wherein the aryl portion may be substituted with alkyl groups having 1 to 24 carbon atoms, and E' is hydrogen or a monovalent group that is substituted on one of the remaining carbon atoms; G and G' each are hydroxy or methoxy, provided one is hydroxy and the other is methoxy; and Z and Z' taken individually represent the moieties to complete the chromophoric system of a triarylmethane dye when said N-containing ring, T, is open and Z and Z' taken together represent the bridged moieties to compete the chromophoric system of a bridged triarylmethane dye when said N-containing ring, T, is open; and (b) in the same or a separate layer, a developing material capable of reducing said Y' moiety whereby said compound is rendered colorless.

18. A image-recording material according to claim 16 wherein said image dye-providing compound is

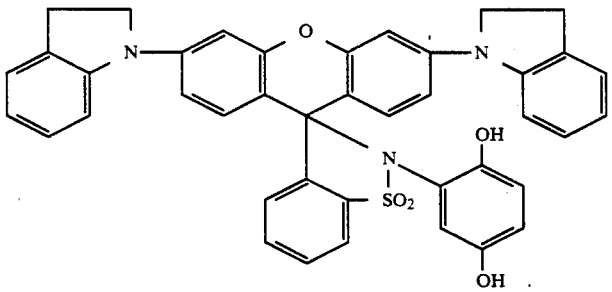

19. An image-recording material according to claim 17 wherein said image dye-providing compound is

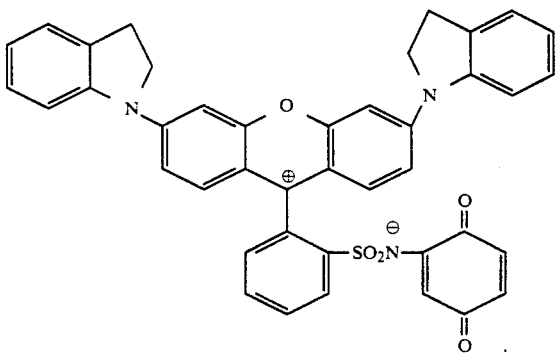

* * * * *

UNITED STATES PATENT AND TRADEMARK OFFICE
CERTIFICATE OF CORRECTION

PATENT NO. : 5,258,279

DATED : November 2, 1993

INVENTOR(S) : M. Simon, M. Kampe, and D. Waller

It is certified that error appears in the above-indentified patent and that said Letters Patent is hereby corrected as shown below:

Col. 30, lines 12-21, (claim 1) delete

"                    Formula I                    "

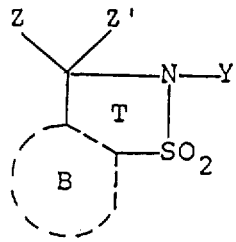

and insert therefor

-- (a) and (b) --

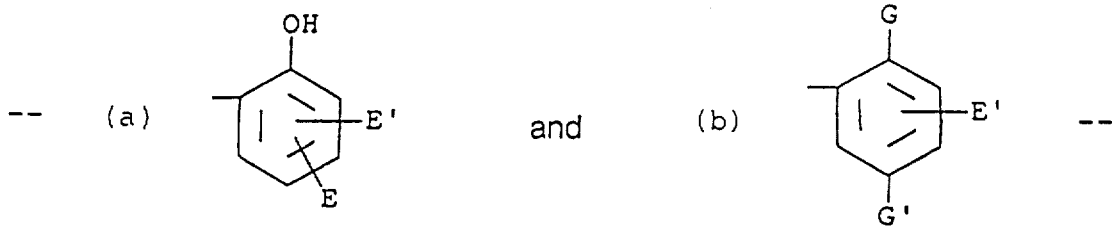

Col. 30, line 68, (claim 5) after "A'" delete --$\pi$--.

UNITED STATES PATENT AND TRADEMARK OFFICE
CERTIFICATE OF CORRECTION

PATENT NO. : 5,258,279

DATED : November 2, 1993

INVENTOR(S) : M. Simon, M. Kampe, and D. Waller

Page 2 of 3

It is certified that error appears in the above-indentified patent and that said Letters Patent is hereby corrected as shown below:

Col. 32, lines 27-35, (claim 16) delete

" 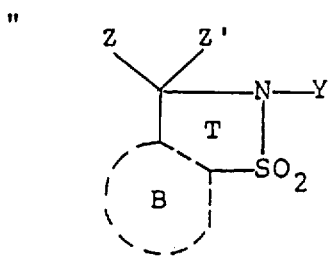 Formula I "

and insert therefor

-- (a) and (b) 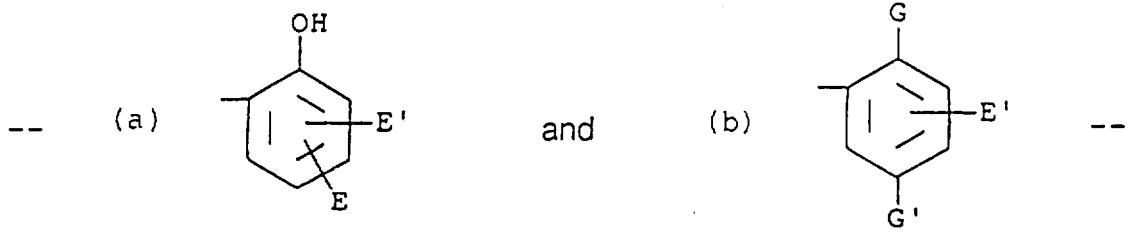 --

UNITED STATES PATENT AND TRADEMARK OFFICE
CERTIFICATE OF CORRECTION

PATENT NO. : 5,258,279
DATED : November 2, 1993
INVENTOR(S) : M. Simon, M. Kampe, and D. Waller It is certified that error appears in the above-indentified patent and that said Letters Patent is hereby corrected as shown below:

Col. 33, lines 4-25, (claim 17), delete

" Formula I "

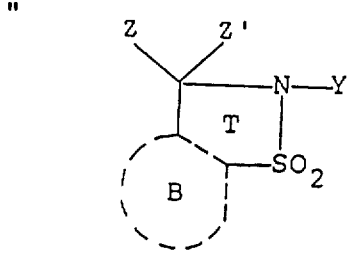

and insert therefor

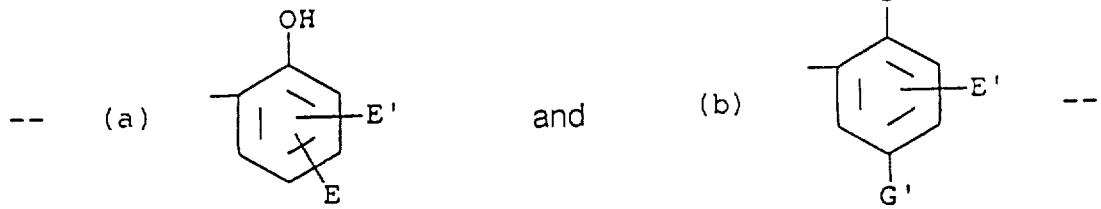

Signed and Sealed this

Twenty-eighth Day of June, 1994

Attest:

BRUCE LEHMAN

Attesting Officer      Commissioner of Patents and Trademarks